(12) United States Patent
Poxon et al.

(10) Patent No.: US 9,592,202 B2
(45) Date of Patent: Mar. 14, 2017

(54) METHOD TO STABILIZE A DIETARY SUPPLEMENT TO FACILITATE JOINT HEALTH IN HUMANS

(75) Inventors: Scott William Poxon, Mechanicsville, VA (US); Denise Lowe Walters, Richmond, VA (US)

(73) Assignee: WYETH LLC, New York, NY (US)

(*) Notice: Subject to any disclaimer, the term of this patent is extended or adjusted under 35 U.S.C. 154(b) by 686 days.

(21) Appl. No.: 12/778,579

(22) Filed: May 12, 2010

(65) Prior Publication Data

US 2010/0291240 A1 Nov. 18, 2010

Related U.S. Application Data

(60) Provisional application No. 61/177,888, filed on May 13, 2009.

(51) Int. Cl.
| | |
|---|---|
| *A61K 33/10* | (2006.01) |
| *A61P 19/02* | (2006.01) |
| *A61P 3/02* | (2006.01) |
| *A61K 9/20* | (2006.01) |
| *A61K 31/7008* | (2006.01) |

(52) U.S. Cl.
CPC .......... *A61K 9/2077* (2013.01); *A61K 9/205* (2013.01); *A61K 9/2027* (2013.01); *A61K 31/7008* (2013.01); *A61K 33/10* (2013.01)

(58) Field of Classification Search
CPC .... A61K 9/2027; A61K 9/205; A61K 9/2077; A61K 31/7008; A61K 33/10; A61K 2300/00
See application file for complete search history.

(56) References Cited

U.S. PATENT DOCUMENTS

| | | | |
|---|---|---|---|
| 2,410,417 A * | 11/1946 | Andersen | 424/459 |
| 3,683,076 A | 8/1972 | Rovati et al. | |
| 3,697,652 A | 10/1972 | Rovati et al. | |
| 4,582,709 A * | 4/1986 | Peters et al. | 426/74 |
| 4,642,340 A | 2/1987 | Senin et al. | |
| 4,786,510 A * | 11/1988 | Nakel et al. | 426/74 |
| 5,364,845 A | 11/1994 | Henderson | |
| 5,587,363 A | 12/1996 | Henderson | |
| 5,840,715 A | 11/1998 | Florio | |
| 5,885,617 A * | 3/1999 | Jordan | 424/474 |
| 5,916,565 A | 6/1999 | Rose et al. | |
| 5,922,692 A | 7/1999 | Marino | |
| 6,492,349 B1 | 12/2002 | Henderson | |
| 2005/0214383 A1 * | 9/2005 | Bubnis et al. | 424/641 |
| 2007/0264329 A1 * | 11/2007 | Stotler et al. | 424/464 |
| 2009/0022792 A1 * | 1/2009 | Dittmar et al. | 424/464 |

FOREIGN PATENT DOCUMENTS

| | | |
|---|---|---|
| EP | 214642 | 3/1987 |
| EP | 444000 | 8/1991 |
| JP | 2001-064159 A2 | 3/2001 |
| WO | WO02/13793 A2 | 2/2002 |
| WO | WO2008/136016 A1 | 11/2008 |

OTHER PUBLICATIONS

Towheed, T.E., Arthritis and Rheumatism, 49, 601-604, (2003).
Perry, G.H., et al., Annals of the Rheumatic Diseases, 31,440-448, (1972).
Shao, Yu, Journal of Pharmaceutical and Biomedical Analysis, 35(2004) pp. 625-631.
Jun, et al., Journal of Agricultural Food and Chemistry, 51(21) p. 6345 (2003).
Lieberman, et al., Pharmaceutical Dosage Forms: Tablets, vol. 1, Second Ed., published by Marcel Dekker, Inc. (1989).
Chou et al., Effects of Chondroitin and Glucosamine Sulfate in a Dietary Bar Formulation on Inflammation, Interleukin-1β, Matrix Metalloprotease-9, and Cartilage Damage in Arthritis, Exp Biol Med (Maywood), vol. 230: pp. 255-262, Apr. 2005.
Hathcock & Shao, Regulatory Toxicology and Pharmacology, vol. 47, pp. 78-83, 2007.
Nakamura et al., Rheum. Int., vol. 27, pp. 213-218, 2007.
Reginster et al., Rheumatology, vol. 46, pp. 731-735, 2007.

* cited by examiner

*Primary Examiner* — Suzanne Ziska
*Assistant Examiner* — Thurman Wheeler
(74) *Attorney, Agent, or Firm* — Jeffrey M. Gold; Maureen P. O'Brien; Paula K. Davis

(57) ABSTRACT

The present invention provides for compositions comprising glucosamine wherein the glucosamine has improved and/or enhanced stability. Additionally, the present invention provides for methods of stabilizing compositions for use in preparing an oral dosage form comprising glucosamine.

18 Claims, 1 Drawing Sheet

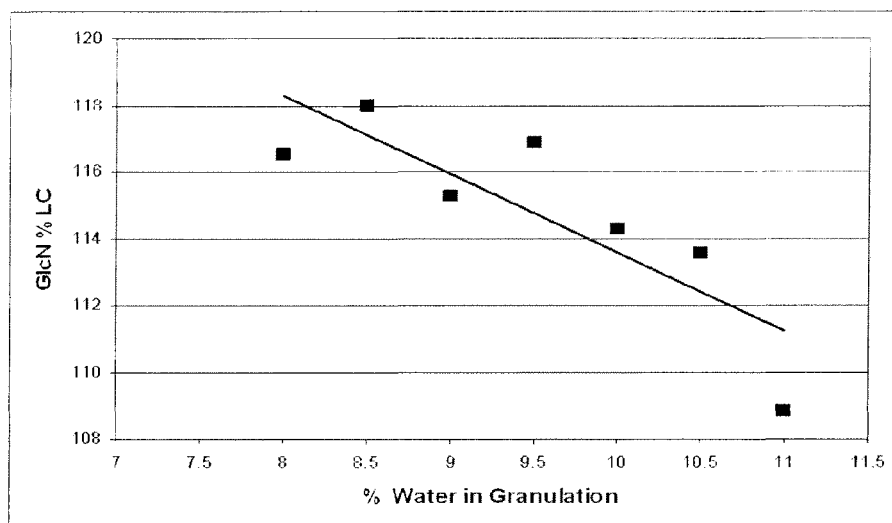
GlcN % LC = Glucosamine % Label Claim

METHOD TO STABILIZE A DIETARY SUPPLEMENT TO FACILITATE JOINT HEALTH IN HUMANS

BACKGROUND OF THE INVENTION

Glucosamine is a valuable pharmacological agent in the treatment of a wide variety of ailments, for example the treatment of osteoarthritic conditions in animals and humans. Glucosamine is a natural substance found in high quantities in joint structures. More specifically, glucosamine 5-phosphate, is naturally occurring within the body and is a component in the biosynthesis of glycosaminoglycans, proteoglycans, hyaluronan and collagen.

The main function of glucosamine in joint structures is to produce cartilage components necessary for maintaining and repair joint tissue. Glucosamine stimulates the formation of joint structural components such as collagen, the protein of the fibrous substances that holds the joints together and helps to build-up the cartilage matrix. Collagen is the main component of the shock-absorbing cushion called articular cartilage. It is also a necessary nutrient in the production of synovial fluid. Some people may lose the ability with age to produce glucosamine, thereby inhibiting the growth of cartilage destroyed during wear and tear in osteoarthritis patients (Towheed, T. E., Arthritis and Rheumatism, 49, 601-604, 2003).

When taken orally as a dietary supplement in the form of glucosamine sulfate, it has been shown to exert protective effect against joint destruction and is selectively used by joint tissues to promote healthy joint function and show potential therapeutic effect in osteoarthritis (Perry, G. H., et al., Ann. Rheum. Dis., 31,440-448, 1972). Glucosamine has also been shown to address the root cause of osteoarthritis disease. It supports the body's natural ability to tackle the disease on its own by providing the building blocks to many structural components such as glucosaminoglycons to repair the damage caused by osteoarthritis.

N-acetylglucosamine, another bioavailable form of glucosamine, does not have any established negative side effects and is a valuable and important component of protein synthesis in the animal body that has a positive effect on tissue regeneration. N-acetylglucosamine has therapeutic potential in the prevention and/or treatment of a wide variety of diseases such as gastritis, food allergies, inflammatory bowel disease (IBD), diverticulitis, acute and chronic forms of rheumatoid arthritis and osteoarthritis, as well as the pathological conditions arising from metabolic disorders of the osteoarticular tissues.

Accordingly, it is well established that nutritional supplements containing glucosamine may be used as therapy for the treatment of connective tissues. U.S. Pat. No. 3,683,076 to Rovati et al. teaches that glucosamine sulfates are useful to treat arthritic conditions. U.S. Pat. No. 3,697,652 to Rovati et al. discloses that N-acetyl glucosamine can be used to treat degenerative afflictions of the joints. U.S. Pat. Nos. 5,364,845, 5,587,363 and 6,492,349 (to Henderson) show that glucosamine, chondroitin and manganese are used to protect and repair connective tissue. In U.S. Pat. No. 5,840,715 to Florio, N-acetyl glucosamine sulfate, chondroitin sulfate, gamma linolenic acid ercosapentaenoic acid and docosahexaneoic acid, and manganese aspartate are combined to treat arthritis symptoms. U.S. Pat. No. 5,916,565 to Rose et al. teaches a composition comprised of D-glucosamine hydrochloride, chondroitin sulfate, cayenne, ginger, turmeric, yucca, Devil's Claw, nettle leaf, Black Cohosh, alfalfa, and celery seeds to repair and maintain damaged tissues in joints of vertebrates. In U.S. Pat. No. 5,922,692, Marino discloses that glucosamine sulfate and chondroitin sulfate can be added to foodstuffs. Lexington, Ky.) for oral administration of hyaluronic acid.

Despite the health benefits associated with glucosamine, there exist several unfavorable properties of this compound as well. Glucosamine is highly hygroscopic and its amino group oxidizes readily. One approach to resolve the stability issues associated with glucosamine, more specifically glucosamine sulphate, is to protect the molecule from contact with oxygen in the form of coated tablets, ampules or capsules. Alternatively, anti-oxidants may be used, such as sodium hyposulphite, to block the oxidation of the amino group. However, neither approach addresses the problem of the hygroscopic nature of glucosamine. This necessitates the preparation of these forms in environments with a very low relative humidity. However, even this approach is less than desirable because the shelf life is practically insufficient for their use.

Additional approaches believed to improve the stability of glucosamine include U.S. Pat. No. 4,642,340 which describes formation of a crystalline mixed salt of glucosamine sulphate with an alkali halide, namely sodium chloride. Formation of a mixed salt increases the chemical stability at ambient temperature and renders the glucosamine sulphate less hygroscopic. EP-214642 describes an improved method for formation of a mixed salt of glucosamine sulphate with alkali halides. Specifically it describes preparation of a mixed salt with potassium chloride. The potassium salt has the advantage of avoiding the disfavorable adiuretic effect of sodium chloride, which is particularly detrimental in case of patients with cardiovascular disease. The mixed salt is essentially stable over 30 days at 75% relative humidity/20° C. EP-444000 describes the stabilization of an oral dosage form of glucosamine sulphate by providing ascorbic acid as an anti-oxidant in an amount being of at least ¼ of that of glucosamine sulphate. Calcium carbonate is required as a desiccant. The formulation is suited for manufacturing oral dosage forms such as tablets, most preferably capsules.

Despite the fact that others have reported formulations and methods that are believed to improve the stability of glucosamine, it has been surprisingly found that the United States Pharmacopoeia (USP) methods do not separate the degradants of glucosamine from pure glucosamine. Yu Shao, in J. Pharm and Biomed Analysis, has published an analytical method that will separate the degradants of glucosamine from pure glucosamine. J Agric Food Chem, 51(21), p 6345 2003. This article identifies potential glucosamine degradants and chemical pathways of degradation. Such glucosamine degradants include 5-(hydroxymethyl)-2-furaldehyde (5-HMF), 2-(tetrahydroxybutyl)-5-(3',4'-dihydroxy-1'-trans-butenyl)pyrazine, 2-(tetrahydroxybutyl)-5-(2',3',4'-trihydroxybutyl)pyrazine, commonly known as deoxyfructosazine and 2,5-bis(tetrahydroxybutyl)pyrazine (fructosazine).

Therefore, it is the inventors' belief that many products in the marketplace that may appear stable by the USP methods are in fact not stable. Testing of commercially available products confirmed that glucosamine degradation products were present. The degradants were especially observed in supplements containing glucosamine, vitamins and minerals. For example, the inventors tested the commercially available products Weil, ArthX-Plus and Joint Strength. Dr. Weil's glucosamine capsules state on the label that it contains glucosamine in an amount of 500 mg. Upon testing with the Yu Shao method however the product was found to contain 88% of the label claim amount of glucosamine. Additionally, the degradant fructosazine was present. Arth-X-Plus, which contains a combination of glucosamine sulphate, calcium hydroxyapatite, and a variety of other vitamins, minerals and other herbal supplements, was also tested utilizing the Yu Shao method and was found to contain glucosamine degradants fructosazine and deoxyfructosazine. Lastly, Joint Strength, which contains Vitamins C, D3, Vitamin K1, Riboflavin, Vitamin B-6, Calcium, Iodine, Magnesium, Zinc, Copper, Manganese, Molybdenum was tested utilizing the Yu Shao method and was found to contain both glucosamine degradant fructosazine and deoxyfructoxazine.

Therefore, many products in the marketplace that may appear stable by the USP methods are in fact not stable and contain degradants. Accordingly, despite prior efforts to stabilize glucosamine, the therapeutic importance of this compound necessitates the need to develop alternate methods of stabilizing glucosamine. The present invention provides a composition that includes glucosamine in a highly storage-stable form. Additionally, the present invention provides for a method of manufacture for highly storage-stable forms of glucosamine containing compositions that will improve the packaged product stability and retention of glucosamine.

SUMMARY OF THE INVENTION

This invention relates to compositions comprising glucosamine and methods of making said glucosamine containing compositions. More specifically, the present invention provides for compositions for use in preparing oral dosage forms comprising glucosamine wherein the glucosamine has improved and/or enhanced stability. Additionally, the present invention provides for methods of stabilizing compositions for use in preparing an oral dosage form comprising glucosamine which includes the steps of providing a granulation comprising a measured amount of glucosamine, wherein the glucosamine is granulated separately from vitamins, minerals and/or other active ingredients thereby improving and/or enhancing the stability of the glucosamine in the presence of such vitamins, minerals and/or other active ingredients.

In one embodiment of the invention there is provided a method for manufacturing a composition comprising glucosamine and calcium comprising the steps of (a) providing a first granulation composition comprising glucosamine, a first disintegrant and a first binder and (b) providing a second granulation composition comprising calcium, a second disintegrant and a second binder; and mixing the first granulation and the second granulation, wherein the composition has improved and/or enhanced shelf stability.

In another embodiment of the invention there is provided a method for manufacturing a composition comprising glucosamine and calcium comprising the steps of (a) providing a first granulation composition comprising glucosamine, a first disintegrant and a first binder and (b) providing a second granulation composition comprising calcium, a second disintegrant and a second binder; and mixing the first granulation and the second granulation, wherein the first granulation is formed in an essentially dry state, and further the composition has improved and/or enhanced shelf stability.

In yet another embodiment of the invention there is provided a method for manufacturing a composition comprising glucosamine and at least one vitamin or at least one mineral comprising: (a) providing a first granulation composition comprising glucosamine, a first disintegrant and a first binder, wherein the pH of the first granulation is no greater than 7 and (b) providing a second granulation composition comprising at least one vitamin, mineral or active ingredient, a second disintegrant and a second binder; and mixing the first granulation and the second granulation, wherein the composition has improved and/or enhanced shelf stability In yet another embodiment of the invention there is provided a method for manufacturing a composition comprising glucosamine and at least one vitamin or at least one mineral comprising: (a) providing a first granulation composition comprising glucosamine, a first disintegrant and a first binder, wherein the pH of the first granulation is no greater than 7 and (b) providing a second granulation composition comprising at least one vitamin, mineral or active ingredient, a second disintegrant and a second binder; and mixing the first granulation and the second granulation, wherein the first granulation is formed in an essentially dry state and further the composition has improved and/or enhanced shelf stability In yet another aspect of the invention there is provided compositions made by any of the methods described herein.

BRIEF DESCRIPTION OF THE DRAWINGS

FIG. 1: Glucosamine HCl stability produced by wet granulation methods

DETAILED DESCRIPTION OF THE INVENTION

The present invention provides for compositions for use in preparing oral dosage forms comprising glucosamine wherein the glucosamine has improved and/or enhanced stability. Additionally, the present invention provides for methods of stabilizing compositions for use in preparing an oral dosage form comprising glucosamine which includes the steps of providing a granulation comprising a measured amount of glucosamine, wherein the glucosamine is granulated separately from vitamins, minerals and/or other active ingredients thereby improving and/or enhancing the stability of the glucosamine in the presence of such vitamins, minerals and/or other active ingredients. As used herein the term glucosamine shall include glucosamine or any salt thereof. Examples of acceptable forms of glucosamine for practice in the compositions and methods described herein, include but not are not limited to glucosamine hydrochloride (HCL), glucosamine sulfate, N-acetyl glucosamine, or any metabolite of the forgoing. Additionally, any therapeutically effective amount of glucosamine may be used in the compositions and methods described herein. Preferably, the therapeutically effective amount of glucosamine is about 1500 mg. This can be administered in a single dose or multiple doses.

In a preferred embodiment, the compositions comprising glucosamine are prepared by providing glucosamine alone or in combination with traditional excipients utilized in the preparation of solid dosage forms. Conventional tableting excipients and the conventional amounts used are described in Lieberman et al., *Pharmaceutical Dosage Forms-Tablets*, volume 1, 2d Ed., published by Marcel Dekker, Inc., in 1989, the text of which is hereby incorporated by reference. Such excipients include but are not limited to absorbents, diluents, flavorants, colorants, stabilizers, fillers, binders, disintegrants, lubricants, wetting agents, glidants, antiadherents, preservatives, buffer, sweeteners, dispersants, thickeners, and solubilizing agents.

Preferably, the glucosamine containing granulation comprises glucosamine, a disintegrant and a binder. Preferably the disintegrant is croscarmellose sodium or crosspovidone. Sodium starch glycolate, starch, and microcrystalline cellulose can also be used. Preferably the binder is polyvinylpyrrolidone, polyvinylpolypyrrolidone; however, other commonly used wet granulation binders include microcrystalline cellulose, cellulose derivatives, povidone, copolyvidone, gelatin, natural gums, starch paste, pregelatinized starch and sucrose. Most preferably the binder is polyvinylpyrrolidone. One skilled in the art would appreciate that the amounts of disintegrant and/or binder depend upon the amount of glucosamine for use in the compositions described herein. In a preferred embodiment the disintegrant is croscarmellose sodium and is present in an amount from about 2 to about 4% w/w. In yet another preferred embodiment the binder is polyvinylpyrrolidone and is present in an amount from about 2 to about 5% w/w.

In light of the fact that glucosamine is a typical ingredient for incorporation into dietary supplements, it is desirable to provide compositions that provide a therapeutic amount of glucosamine in combination with vitamins, minerals and/or other active ingredients. In a preferred embodiment, the composition comprises a therapeutically effective amount of glucosamine and a therapeutically effective amount of calcium, wherein the glucosamine is provided in a first granulation and the calcium is provided in a second granulation. As used herein, the term calcium shall include, but not be limited to pharmaceutically acceptable calcium compounds such as calcium carbonate, dibasic calcium phosphate, tribasic calcium phosphate, calcium gluconate, calcium lactate, calcium citrate, and combinations thereof. In a preferred embodiment, the composition comprises calcium carbonate. In a preferred embodiment, the therapeutically effective amount of calcium carbonate is about 1200 mg. This can be administered in a single dose or multiple doses.

Typically, those skilled in the art prefer to combine multiple ingredients into a single granulation to improve the chemical content uniformity in the finished dosage form. However, in the case of glucosamine HCL and calcium carbonate, the inventors have found this is not the preferred formulation and manufacturing approach. As both calcium carbonate and glucosamine HCL are poorly flowing and poorly compressible powders in their chemically pure states, it is preferable to wet granulation these materials. The inventors have found that when calcium carbonate is granulated in an admixture with glucosamine HCl the composition exhibited poor stability. More specifically, the inventors surprisingly found that in the presence of water as the granulation fluid, compositions comprising glucosamine HCL and calcium carbonate in an admixture retained less than 80% of pure glucosamine stored for 3 months at 40° C./75% relative humidity. The inventors believe without wishing to be bound to any theory that the slurry pH of the glucosamine HCl, calcium carbonate and water admixture has a basic pH whereas the slurry pH of glucosamine and water alone is acidic. Therefore stability of such glucosamine HCl containing compositions is preferred to be at lower pH.

Accordingly, in a preferred embodiment, is provided a method for manufacturing a compositions comprising glucosamine and calcium comprising the steps of (a) providing a first granulation composition comprising glucosamine, a first disintegrant and a first binder and (b) providing a second granulation composition comprising calcium, a second disintegrant and a second binder; and mixing the first granulation and the second granulation. The inventors believe, without being bound to any theory that separately granulating the calcium and glucosamine physically coats the granules with the granulation excipients and sterically separates these compounds inside the tablet leading to improved solid-state long-term shelf stability.

One skilled in the art would appreciate that the granulations described can be prepared by conventional granulation methods include wet granulation, dry granulation. In a preferred embodiment, the granulations described herein are prepared by wet granulation. The inventors have found that in addition to pH, glucosamine degradation is correlated to % w/w of the granulation fluid used in the manufacture of the wet granulated glucosamine compositions. More specifically, it has been found that the glucosamine containing granulation should be processed in an essentially dry state. As used herein, "an essentially dry state" shall mean preferably less than 3% w/w granulation fluid. Examples of granulation fluids include water or alcohol, preferably ethanol. Accordingly in preferred embodiment, the glucosamine granulation composition comprises glucosamine, a disintegrant, a binder and water, wherein the amount of granulation fluid is less than 3% w/w of the granulation. In an even more preferred embodiment, the granulation fluid is water.

Additional ingredients may optionally be included in the compositions and methods described herein. Examples of such ingredients include but are not limited to vitamins such as vitamin A, vitamin A precursor beta-carotene, vitamin K, vitamin C, vitamin D, vitamin E, thiamine, riboflavin, niacin, vitamin B6, folic acid, vitamin B12, biotin, and pantothenic acid; minerals such as iron, phosphorus, iodine, magnesium, zinc, copper, manganese, chromium, molybdenum, manganese, and boron. When incorporating such additional ingredients, consideration of the pH of the slurry that would be formed upon admixing with glucosamine. In order to enhance the stability of the glucosamine, the glucosamine granulation slurry should be no greater than a pH of 7. Therefore, if addition of the optional ingredient would render the glucosamine slurry basic, then the optional ingredient should be granulated separately. Accordingly, in a preferred embodiment, the glucosamine containing vitamin, mineral or other active ingredient composition is prepared by the following method: (a) providing a first granulation composition comprising glucosamine, a first disintegrant and a first binder, wherein the pH of the first granulation is no greater than 7 and (b) providing a second granulation composition comprising at least one vitamin, mineral or active ingredient, a second disintegrant and a second binder; and mixing the first granulation and the second granulation. In yet an even more preferred embodiment, the first granulation composition comprising glucosamine should be granulated in essentially a dry state.

The glucosamine containing granulation as described herein can be directly compressed into any variety of pharmaceutically acceptable solid dosage forms, including tablets and/or caplets. The tablets and/or caplets are preferably coated. Examples of acceptable coatings include polyvinyl alcohol based aqueous film-coat. A polyvinyl alcohol (PVA) coating may be used to limit moisture uptake and improve stability. The inventors believe, without wishing to be bound to any theory that coating said glucosamine containing tablets not only helps to improve swallowability but also blocks moisture uptake into the tablet core to improve solid state long term shelf stability.

EXAMPLES

Example 1

A granulation comprising glucosamine HCL, croscarmellose sodium and 2.8% w/w was prepared utilizing a high sheer mixer and a fluid bed dryer.

Example 2

A granulation comprising calcium carbonate, croscarmellose sodium, povidone and 21% w/w water was prepared utilizing a high sheer mixer and a fluid bed dryer.

Example 3

The granulations of example 1 and example 2 were blended and compressed into tablets. Stability testing was conducted on the finished dosage forms that contained the two separately formed granulations. The percent retained glucosamine after 3 months storage at 40° C. and 75% relative humidity was approximately 100% with no glucosamine degradant products detected. When compared to a tablet where the glucosamine HCL and calcium carbonate were granulated together, the percent retained glucosamine after 3 months storage at 40° C. and 75% relative humidity was less than approximately 80%. Accordingly, preparing a granulation wherein the glucosamine is granulated in a first granulation and the calcium carbonate is granulated in a second granulation and the granulations are subsequently mixed and compressed into tablets results in a dosage form with improved stability and less degradation.

Example 4

To evaluate the effect of moisture and pH, compressed and coated tablets were prepared using the following changes in manufacturing procedure 1) calcium with glucosamine co-granulated with calcium carbonate, (CGC), high moisture, high pH, 2) glucosamine co-granulated with calcium carbonate, (CGC), low moisture, high pH, 3) glucosamine granulated separately from calcium carbonated (SG), low moisture, low pH. All combinations were analyzed for glucosamine potency shortly after manufacture. Tablets were then stored at 40° C./75% RH and evaluated for stability for various time points. Samples were analyzed with a modified stability indicating literature method for glucosamine.
Results: Combination 1 showed a potency loss of 81% of target at initial contained two dimerization products (fructosazine and deoxyfructosazine). There was no substantial change in glucosamine potency over 6 months. Combination 2 gave a potency of 92% of target at initial, contained fructosazine, deoxyfructosazine and a third unidentified peak. Stability was not continued with combination 2. Combination 3 gave a potency of 95% of target initial with no degradation/dimerization peaks. Combination 3 was evaluated for 9 months at 40° C./75% RH and showed the development (fructosazine and deoxyfructosazine), but showed no substantial potency loss though 9 months of accelerated stability.

The invention claimed is:

1. A method for manufacturing a composition comprising a therapeutically effective amount of glucosamine and a therapeutically effective amount of calcium wherein the glucosamine is granulated separately apart from the calcium and the calcium is granulated separately apart from the glucosamine, comprising the steps of (a) providing a first granulation composition comprising glucosamine, a first disintegrant and a first binder and (b) providing a second granulation composition comprising calcium, a second disintegrant and a second binder; and mixing the first granulation and the second granulation, wherein the composition has improved and/or enhanced shelf stability; wherein the calcium is selected from calcium carbonate, dibasic calcium phosphate, tribasic calcium phosphate, calcium gluconate, calcium lactate, calcium citrate, and combinations thereof; and wherein the therapeutically effective amount of glucosamine and the therapeutically effective amount of calcium is administered in a single dose or multiple doses.

2. A method for manufacturing a composition comprising a therapeutically effective amount of glucosamine and a therapeutically effective amount of calcium wherein the glucosamine is granulated separately apart from the calcium and the calcium is granulated separately apart from the glucosamine, comprising the steps of (a) providing a first granulation composition comprising glucosamine, a first disintegrant and a first binder and (b) providing a second granulation composition comprising calcium, a second disintegrant and a second binder; and mixing the first granulation and the second granulation, wherein the first granulation is formed in less than 3% w/w granulation fluid, wherein the calcium is selected from calcium carbonate, dibasic calcium phosphate, tribasic calcium phosphate, calcium gluconate, calcium lactate, calcium citrate, and combinations thereof; further the composition has improved and/or enhanced shelf stability; and wherein the therapeutically effective amount of glucosamine and the therapeutically effective amount of calcium is administered in a single dose or multiple doses.

3. The method according to claim 1 wherein the pH of the first granulation is no greater than 7 and the second granulation composition further comprises at least one vitamin, mineral or active ingredient.

4. The method according to claim 3 wherein the first granulation is formed in less than 3% w/w granulation fluid.

5. The method according to claim 1 further comprising compressing the composition into a tablet or caplet.

6. The method of claim 5 further comprising coating the tablet or caplet with a pharmaceutically acceptable coating material.

7. The method of claim 6 wherein the coating material comprises is polyvinyl alcohol.

8. The method according to claim 1 wherein the first disintegrant is croscarmellose sodium and the first binder is polyvinylpyrrolidone.

9. A method for manufacturing a composition comprising a therapeutically effective amount of glucosamine and a therapeutically effective amount of calcium wherein the glucosamine is granulated separately apart from the calcium and the calcium is granulated separately apart from the glucosamine, comprising the steps of: (a) wet granulating a first granulation composition comprising glucosamine, a first disintegrant and a first binder using less than 3% by weight of granulation fluid, at a pH no greater than 7, and (b) wet granulating a second granulation composition comprising calcium, a second disintegrant, a second binder and at least one vitamin, mineral or active ingredient; and (c) mixing the first granulation and the second granulation, wherein the composition has improved and/or enhanced shelf stability; wherein the calcium is selected from calcium carbonate, dibasic calcium phosphate, tribasic calcium phosphate, calcium gluconate, calcium lactate, calcium citrate, and combinations thereof; and wherein the therapeutically effective amount of glucosamine and the therapeutically effective amount of calcium is administered in a single dose or multiple doses.

10. The method of claim 9 wherein at least one of the first disintegrant or second disintegrant is croscarmellose sodium.

11. The method of claim 10 wherein croscarmellose sodium comprises from about 2% to about 4% of the weight of the first granulation composition.

12. The method of claim 9 wherein at least one of the first binder or second binder is polyvinylpyrrolidone.

13. The method of claim 12 wherein the polyvinylpyrrolidone comprises from about 2% to about 5% of the weight of the first granulation composition.

14. The method of claim 9 further comprising compressing the composition into a tablet or caplet.

15. The method of claim 5 further comprising coating the tablet or caplet with a pharmaceutically acceptable coating material comprising polyvinyl alcohol.

16. The method of claim 1, wherein multiple doses are two doses, three doses, four doses, or five doses.

17. The method of claim 2, wherein multiple doses are two doses, three doses, four doses, or five doses.

18. The method of claim 9, wherein multiple doses are two doses, three doses, four doses, or five doses.

* * * * *